(12) United States Patent
Lyssikatos et al.

(10) Patent No.: US 6,645,982 B2
(45) Date of Patent: Nov. 11, 2003

(54) CRYSTAL FORMS OF 6-[(4-CHLORO-PHENYL)-HYDROXY-(3-METHYL-3H-IMIDAZOL-4-YL)-METHYL]-4-(3-ETHYNYL-PHENYL)-1-METHYL-1H-QUINOLIN-2-ONE, 2,3-DIHYDROXYBUTANEDIOATE SALTS AND METHOD OF PRODUCTION

(75) Inventors: Joseph P. Lyssikatos, Superior, CO (US); Derek L. Tickner, Waterford, CT (US); Linda S. Newton, New London, CT (US); Zheng J. Li, Quaker Hill, CT (US); Clifford N. Meltz, Niantic, CT (US)

(73) Assignee: Pfizer Inc, New York, NY (US)

( * ) Notice: Subject to any disclaimer, the term of this patent is extended or adjusted under 35 U.S.C. 154(b) by 13 days.

(21) Appl. No.: 10/021,201

(22) Filed: Dec. 7, 2001

(65) Prior Publication Data

US 2003/0032653 A1 Feb. 13, 2003

Related U.S. Application Data

(60) Provisional application No. 60/256,598, filed on Dec. 19, 2000.

(51) Int. Cl.[7] ..................... A61K 31/47; C07D 215/227
(52) U.S. Cl. .................. 514/312; 546/157; 546/158
(58) Field of Search ............... 514/312; 546/157, 546/158

(56) References Cited

U.S. PATENT DOCUMENTS

| | | |
|---|---|---|
| 5,747,498 A | 5/1998 | Schnur et al. |
| 5,968,952 A | 10/1999 | Venet et al. |
| 6,037,350 A | 3/2000 | Venet et al. |
| 6,040,334 A | 3/2000 | Myers et al. |
| 6,071,935 A | 6/2000 | Lyssikatos |
| 6,083,985 A | 7/2000 | Yonemoto et al. |
| 6,150,377 A | 11/2000 | Lyssikatos et al. |

FOREIGN PATENT DOCUMENTS

| | | |
|---|---|---|
| EP | 0856315 A1 | 8/1996 |
| WO | 9705902 | 2/1997 |
| WO | 9716443 | 5/1997 |
| WO | 9721701 | 6/1997 |
| WO | 9857633 | 12/1998 |
| WO | 0016778 | 3/2000 |

*Primary Examiner*—Patricia L. Morris
(74) *Attorney, Agent, or Firm*—Peter C. Richardson; Paul H. Ginsburg; Adrian G. Looney (57) ABSTRACT

The invention relates to crystal forms of 6-[(4-chloro-phenyl)-hydroxy-(3-methyl-3H-imidazol-4-yl)-methyl]-4-(3-ethynyl-phenyl)-1-methyl-1H-quinolin-2-one, 2,3-dihydroxy butanedioate salts having the formula shown below:

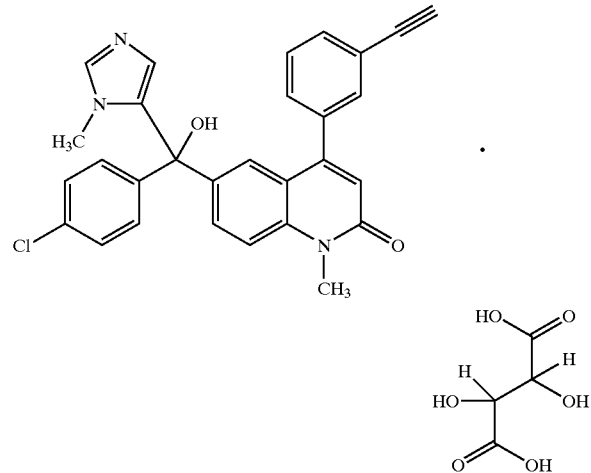

formula I and to pharmaceutical compositions containing the above compound, methods of treating hyperproliferative diseases, such as cancers, in mammals, especially humans by administering the above compound, and to methods of preparing the crystal forms of the above compound and related compounds.

26 Claims, 2 Drawing Sheets

CRYSTAL FORMS OF 6-[(4-CHLORO-PHENYL)-HYDROXY-(3-METHYL-3H-IMIDAZOL-4-YL)-METHYL]-4-(3-ETHYNYL-PHENYL)-1-METHYL-1H-QUINOLIN-2-ONE, 2,3-DIHYDROXYBUTANEDIOATE SALTS AND METHOD OF PRODUCTION

The application claims the benefit of U.S. Provisional Patent Application No. 60/256,598, filed Dec. 19, 2000, which is hereby incorporated b reference in its entirety.

BACKGROUND OF THE INVENTION

This invention relates to crystal forms of 6-[(4-chloro-phenyl)-hydroxy-(3-methyl-3H-imidazol-4-yl)-methyl]-4-(3-ethynyl-phenyl)-1-methyl-1H-quinolin-2-one, 2,3-dihydroxy butanedioate (1:1) salts having the formula shown below:

formula I

The invention further relates to a method of making 6-[(4-chloro-phenyl)-hydroxy-(3-methyl-3H-imidazol-4-yl)-methyl]-4-(3-ethynyl-phenyl)-1-methyl-1H-quinolin-2-one, 2,3-dihydroxybutanedioate (1:1) salts. The compounds of the present invention are useful in the treatment of hyperproliferative diseases, such as cancers, in mammals, especially humans. The invention further relates to pharmaceutical compositions containing such compounds.

The free base, 6-[(4-chloro-phenyl)-hydroxy-(3-methyl-3H-imidazol-4-yl)-methyl]-4-(3-ethynyl-phenyl)-1-methyl-1H-quinolin-2-one, is described in co-pending U.S. Ser. No. 09/383,755, filed Aug. 26, 1999, the disclosure of which is hereby incorporated herein by reference in its entirety. The foregoing application is assigned in common with the present application. The aforementioned free base is useful in the treatment of hyperproliferative diseases such as cancers.

SUMMARY OF THE INVENTION

The present invention relates to crystalline tartrate salts of 6-[(4-chloro-phenyl)-hydroxy-(3-methyl-3H-imidazol-4-yl)-methyl]-4-(3-ethynyl-phenyl)-1-methyl-1H-quinolin-2-one having the formula shown below:

formula I

Two crystal forms of formula I have been identified. The crystal forms of formula I are herein referred to as crystal form A and crystal form B. Crystal form A is an anhydrous crystalline salt of formula 1, while crystal form B is a sesquihydrate crystalline salt of formula 1.

The present invention relates to 6-[(4-chloro-phenyl)-hydroxy-(3-methyl-3H-imidazol-4-yl)-methyl]-4-(3-ethynyl-phenyl)-1-methyl-1H-quinolin-2-one, 2,3-dihydroxy butanedioate salts. The 6-[(4-chloro-phenyl)-hydroxy-(3-methyl-3H-imidazol-4-yl)-methyl]-4-(3-ethynyl-phenyl))-1-methyl-1H-quinolin-2-one has a chiral center at the 6-postion. Thus, the free base, 6-[(4-chloro-phenyl)-hydroxy-(3-methyl-3H-imidazol-4-yl)-methyl]-4-(3-ethynyl-phenyl)-1-methyl-1H-quinol in-2-one, may have specific rotations of (+) or (−). The tartrate salt may be L-tartaric acid or D-tartaric acid. L-tartaric acid is also known as (2R,3R)-(+)-tartaric acid, while D-tartaric acid is (2S,3S)-(−)-tartaric acid. Both acids are available from Aldrich Chemical Company, Inc., Milwaukee, Wis.

Particularly preferred salts include (+)-6-[(4-chloro-phenyl)-hydroxy-(3-methyl-3H-imidazol-4-yl)-methyl]-4-(3-ethynyl-phenyl)-1-methyl-1H-quinolin-2-one, 2,3-dihydroxy butanedioate salt and (−)-6-[(4-chloro-phenyl)-hydroxy-(3-methyl-3H-imidazol-4-yl)-methyl]-4-(3-ethynyl-phenyl)-1-methyl-1H-quinolin-2-one, 2,3-dihydroxy butanedioate salt. Other particularly preferred salts include 6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxy butanedioate salt and 6-[(4-chloro-phenyl)-hydroxy-(3-methyl-3H-imidazol-4-yl)-methyl]-4-(3-ethynyl-phenyl)-1-methyl-1H-quinolin-2-one, (+)-2,3-dihydroxy butanedioate salt.

More particularly preferred salts include (+)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxy butanedioate salt and (−)-6-[(4-chloro-phenyl)-hydroxy-(3-methyl-3H-imidazol-4-yl)-methyl]-4-(3-ethynyl-phenyl)-1-methyl-1H-quinolin-2-one, (+)-2,3-dihydroxy butanedioate salt. The salts of the present invention may be present in anhydrous or hydrous form.

The present invention further relates to (+)-6-[(4-chloro-phenyl)-hydroxy-(3-methyl-3H-imidazol-4-yl)-methyl]-4-(3-ethynyl-phenyl)-1-methyl-1H-quinolin-2-one, (+)-2,3-dihydroxy butanedioate salt. The invention also relates to (−)-6-[(4-chloro-phenyl)-hydroxy-(3-methyl-3H-imidazol- 4-yl)-methyl]-4-(3-ethynyl-phenyl)-1-methyl-1H-quinolin-2-one, (−)-2,3-dihydroxy butanedioate salt.

The present invention further comprises pharmaceutical compositions of crystal forms A and B of the compound of formula I and a method for the production of crystal forms A and B of the compound of formula I.

It is a further object of the present invention to provide crystal forms A and B in a pharmaceutically orally administered composition. Crystal forms A and B of the compound of formula I are useful for the oral administration of the drug in solid form, such as tablets. Crystal form A is preferred for use in the preparation of pharmaceutical compositions containing the compound of formula I in tablet form for oral administration.

Crystal forms A and B have been characterized by powder X-ray diffractometry. The anhydrous crystal form of the present invention is identified in this application as crystal form A. The second crystal form of formula I is a sesquihydrate having approximately 5.5% water and is identified herein as crystal form B.

The anhydrous crystal form A of (+)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxy butanedioate is characterized by high-intensity diffraction peaks at diffraction angles (2θ) of about 3.6, 17.2, 17.6, 18.8, 19.2, 20.4 and 22.1 in a powder X-ray diffraction pattern. The experimental conditions under which the powder X-ray diffraction was conducted are as follows: Cu anode; wavelength 1: 1.54056; wavelength 2: 1.54439 (Rel Intensity: 0.500); range #1-coupled: 3.000 to 40.000; step size: 0.040; step time: 1.00; smoothing width: 0.300; and threshold: 1.0. The characteristic diffraction peaks at diffraction angles (2θ) in a powder X-ray diffraction analysis for the crystal form A are shown in Table 1.

The hydrate crystal form B of (+)-6-[(4-chloro-phenyl)-hydroxy-(3-methyl-3H-imidazol-4-yl)-methyl]-4-(3-ethynyl-phenyl)-1-methyl-1-H-quinolin-2-one, (−)-2,3-dihydroxy butanedioate is characterized in that the crystal provides high-intensity diffraction peaks at diffraction angles (2θ) of about 5.1, 8.1, 18.2, 18.8, 20.2, 20.8, 23.6, 25.8 and 26.0 in a powder X-ray diffraction pattern. The experimental conditions under which the powder X-ray diffraction was conducted are as follows: Cu anode; wavelength 1: 1.54056; wavelength 2: 1.54439 (Rel Intensity: 0.500); range #1-coupled: 3.000 to 40.000; step size: 0.040; step time: 1.00; smoothing width: 0.300; and threshold: 1.0. The characteristic diffraction peaks at diffraction angles (2θ) in a powder X-ray diffraction analysis for crystal form B are shown in Table 2.

The characteristic d-spacings, intensities, and 2-theta (2θ) values for the diffraction pattern of crystal forms A and B are shown below in Tables 1 and 2, respectively.

TABLE 1

Crystal Form A

| Angle 2 theta | d-value Å | I* (rel.) | Angle 2 theta | d-value Å | I* (rel.) | Angle 2 theta | d-value Å | I* (rel.) |
|---|---|---|---|---|---|---|---|---|
| 3.6 | 24.7 | 100 | 16.9 | 5.3 | 1.3 | 23.4 | 3.8 | 2.4 |
| 6.2 | 14.2 | 3.3 | 17.2 | 5.2 | 9.7 | 25.1 | 3.5 | 3.7 |
| 7.2 | 12.3 | 1.9 | 17.6 | 5.1 | 9.2 | 25.5 | 3.5 | 2.0 |
| 9.5 | 9.3 | 1.5 | 18.8 | 4.7 | 5.6 | 26.0 | 3.4 | 1.5 |
| 10.8 | 8.2 | 1.7 | 19.2 | 4.6 | 5.2 | 26.7 | 3.3 | 2.2 |
| 12.3 | 7.2 | 1.2 | 19.7 | 4.5 | 2.0 | 27.6 | 3.2 | 1.8 |

TABLE 1-continued

Crystal Form A

| Angle 2 theta | d-value Å | I* (rel.) | Angle 2 theta | d-value Å | I* (rel.) | Angle 2 theta | d-value Å | I* (rel.) |
|---|---|---|---|---|---|---|---|---|
| 12.5 | 7.1 | 1.4 | 20.4 | 4.4 | 10.0 | 28.2 | 3.2 | 2.0 |
| 13.8 | 6.4 | 1.3 | 21.7 | 4.1 | 1.3 | 28.5 | 3.1 | 2.1 |
| 14.5 | 6.1 | 1.4 | 22.1 | 4.0 | 6.0 | 29.0 | 3.1 | 1.8 |
| 16.0 | 5.5 | 4.8 | 22.6 | 3.9 | 2.2 | 29.9 | 3.0 | 2.0 |

*The relative intensities may change depending on the crystal size and morphology.

TABLE 2

Crystal Form B

| Angle 2 theta | d-value Å | I* (rel.) | Angle 2 theta | d-value Å | I* (rel.) | Angle 2 theta | d-value Å | I* (rel.) |
|---|---|---|---|---|---|---|---|---|
| 5.1 | 17.2 | 45 | 19.9 | 4.5 | 28.5 | 26.0 | 3.4 | 42.9 |
| 8.1 | 10.9 | 30 | 20.2 | 4.4 | 45.3 | 26.7 | 3.3 | 10.4 |
| 12.7 | 7.0 | 10.1 | 20.8 | 4.3 | 100 | 27.6 | 3.2 | 11.0 |
| 13.9 | 6.4 | 20.7 | 21.4 | 4.2 | 20.3 | 28.1 | 3.2 | 10.5 |
| 14.6 | 6.1 | 28.0 | 21.7 | 4.1 | 16.5 | 28.7 | 3.1 | 13.4 |
| 15.2 | 5.9 | 17.2 | 22.8 | 3.9 | 20.8 | 30.2 | 3.0 | 25.9 |
| 15.3 | 5.8 | 11.9 | 23.6 | 3.8 | 39.3 | 31.2 | 2.9 | 10.3 |
| 16.4 | 5.4 | 20.6 | 24.1 | 3.7 | 19.2 | 32.1 | 2.8 | 16.6 |
| 16.8 | 5.3 | 12.1 | 24.4 | 3.6 | 19.6 | 33.1 | 2.7 | 11.2 |
| 18.2 | 4.9 | 29.3 | 24.8 | 3.6 | 13.2 | 34.4 | 2.6 | 10.1 |
| 18.8 | 4.7 | 57.7 | 25.5 | 3.5 | 13.2 | 36.8 | 2.4 | 9.4 |
| 19.3 | 4.6 | 9.6 | 25.8 | 3.5 | 42.3 | 37.4 | 2.4 | 9.4 |

*The relative intensities may change depending on the crystal size and morphology.

It is to be understood that the powder X-ray diffraction pattern is only one of many ways to characterize the arrangement of atoms comprising 6-[(4-chloro-phenyl)-hydroxy-(3-methyl-3H-imidazol-4-yl)-methyl]-4-(3-ethynyl-phenyl)-1-methyl-1H-quinolin-2-one, 2,3-dihydroxy butanedioate and that other methods well known in the art, e.g. single crystal X-ray diffraction, Near Infrared Spectroscopy, etc. may be used to identify crystal forms A and B.

The present invention relates to a compound which is crystal form A of the compound (+)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxy butanedioate or (−)-6-[(4-chloro-phenyl)-hydroxy-(3-methyl-3H-imidazol-4-yl)-methyl]-4-(3-ethynyl-phenyl)-1-methyl-1H-quinolin-2-one, (+)-2,3-dihydroxy butanedioate that exhibits a powder X-ray diffraction pattern having characteristic peaks expressed in degrees 2-theta at approximately 3.6, 6.2, 7.2, 9.5, 10.8, 17.2, 17.6, 19.2, and 22.1. This invention also relates to a crystal of (+)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxy butanedioate or (−)-6-[(4-chloro-phenyl)-hydroxy-(3-methyl-3H-imidazol-4-yl)-methyl]-4-(3-ethynyl-phenyl)-1-methyl-1H-quinolin-2-one, (+)-2,3-dihydroxy butanedioate that exhibits a powder X-ray diffraction pattern having characteristic peaks expressed in degrees 2-theta at approximately the values shown in Table 1 above.

The present invention relates to a compound which is crystal form B of the compound (+)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxy butanedioate or (−)-6-[(4-chloro-phenyl)- hydroxy-(3-methyl-3H-imidazol-4-yl)-methyl]-4-(3-ethynyl-phenyl)-1-methyl-1H-quinolin-2-one, (+)-2,3-dihydroxy butanedioate that exhibits a powder X-ray diffraction pattern having characteristic peaks expressed in degrees 2-theta at approximately 5.1, 8.1, 16.4, 18.2, 20.8, 21.4, 21.7, 24.4, 30.2, 32.1, 36.8 and 37.4. This invention also relates to a crystal of (+)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxy butanedioate or (−)-6-[(4-chloro-phenyl)-hydroxy-(3-methyl-3H-imidazol-4-yl)-methyl]-4-(3-ethynyl-phenyl)-1-methyl-1H-quinolin-2-one, (+)-2,3-dihydroxy butanedioate that exhibits a powder X-ray diffraction pattern having characteristic peaks expressed in degrees 2-theta at approximately the values shown in Table 2 above.

The invention also relates to a process for the preparation of the compounds of the formula I. The free base of formula I is prepared according to the manner described in Example 1. The free base has one chiral carbon at the 6-position. Example 2 discloses the method and process for preparation and separation the two enantiomers of the free base, 6-[(4-chloro-phenyl)-hydroxy-(3-methyl-3H-imidazol-4-yl)-methyl]-4-(3-ethynyl-phenyl)-1-methyl-1H-quinolin-2-one. The faster eluting enantiomer A causes the plane of polarization to rotate in counterclockwise (negative) direction, i.e., (−) enantiomer. While, the slower moving enantiomer B causes the plane of polarization to rotate in clockwise (positive) direction, i.e., (+) enantiomer.

The tartrate salts of the compound of formula I are made by mixing desired tartaric acid (i.e., D or L) with the free base 6-[(4-chloro-phenyl)-hydroxy-(3-methyl-3H-imidazol-4-yl)-methyl]-4-(3-ethynyl-phenyl)-1-methyl-1H-quinolin-2-one. The free base may be either the (−) or (+) enantiomer. The reaction to form crystal form B is done in a mixed solvent system, such as THF/water. Recrystallization of the tartaric salt of formula I in an organic solvent, such as ethyl acetate, at elevated temperatures results in the isolation of crystal form A.

In one preferred embodiment crystal form B is prepared according to the method comprising the steps of (i) charging a flask with free base of the compound of formula I and a solvent; (ii) addition of the tartrate salt to the free base solution followed by stirring to form a thick slurry; and (iii) isolation of the solids by filtration followed by drying. The aforementioned method to prepare crystal form B may be modified to make crystal form A. Following formation of the thick slurry in step (ii) dry ethyl acetate is added to the reaction flask and the stirred supension is atmospherically distilled. As solvent is distilled off fresh ethyl acetate is added, followed by distillation to a small volume. The reaction mixture is then granulated at ambient temperature followed by isolation of the solids (crystal form A) using filtration and vacuum drying.

Crystal form A of the present invention can be produced from isolated crystal form B. Crystal form A is produced by the steps of (i) heating the crystalline form B in an organic solvent, such as ethyl acetate; (ii) removing the water azeotropically followed by replacement with dry ethyl acetate; (iii) removing the solvent under atmospheric conditions to isolate the solids; and (iv) washing the solids using ethyl acetate and subjecting the product to vacuum drying at elevated temperatures, e.g., 40° C. Note that it is also possible to remove the solvent in step (iii) under vacuum.

Crystal form A of the present invention may also be prepared directly without isolation of the crystal form B. For example, crystal form A may be produced by refluxing at 80° C.–82° C. for 1-hour a mixture of the free base of the compound of formula I (approximately 1.3 equivalents) with the tartrate salt in hot 2B ethanol (20 volume). The mixture is allowed to cool to room temperature slowly followed by stirring overnight. The solvent is then removed under atmospheric conditions and the isolated solid is dried.

The salts of the present invention may exist in amorphous form. Although, such forms may be unstable. However, such salts may be converted to crystalline forms according to methods well known to those of ordinary skill in the art, e.g., heating, etc.

It is to be understood that the methods described herein are only exemplary and are not intended to exclude variations in the above parameters which allow the production of crystal forms A and B in varying granulations and yields, according to the desired storage, handling and manufacturing applications of the compound. Crystal forms of the present invention may be further processed, such as granulation or milling, to form microcrystalline material suitable for bulk manufacturing purposes.

The crystal forms A and B can be characterized using powder X-ray diffractometry.

This invention also relates to a method for the treatment of abnormal cell growth in a mammal, including a human, comprising administering to said mammal an amount of a compound of the formula I, as defined above, a prodrug or solvate thereof, that is effective in inhibiting farnesyl protein transferase. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal, including a human, comprising administering to said mammal an amount of a compound of the formula I, as defined above, a prodrug or solvate thereof, that is effective in treating abnormal cell growth.

This invention also relates to a method for the treatment of abnormal cell growth in a mammal which comprises administering to said mammal a therapeutically effective amount of a compound of formula I, a prodrug or solvate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The present invention also relates to a method for the treatment of an infection in a mammal, including a human, that is facilitated by farnesyl protein transferase, such as hepatitus delta virus or malaria, which comprises administering to said mammal a therapeutically effective amount of a compound of formula I as defined above, a prodrug or solvate thereof.

This invention also relates to a pharmaceutical composition for the treatment of abnormal cell growth in a mammal, including a human, comprising an amount of a compound of the formula I, as defined above, a prodrug or solvate thereof, that is effective in inhibiting farnesyl protein transferase, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

This invention also relates to a pharmaceutical composition for the treatment of abnormal cell growth in a mammal, including a human, comprising an amount of a compound of the formula I, as defined above, a prodrug or solvate thereof, that is effective in treating abnormal cell growth, and a pharmaceutically acceptable carrier.

The invention also relates to a pharmaceutical composition for the treatment of abnormal cell growth in a mammal, including a human, which comprises a therapeutically effective amount of a compound of formula I, as defined above, a prodrug or solvate thereof, in combination with a pharmaceutically acceptable carrier and an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

This invention also relates to a pharmaceutical composition for the treatment of an infection in a mammal, including a human, that is facilitated by farnesyl protein transferase, such as malaria or hepatitus delta virus, comprising an amount of a compound of the formula I, as defined above, a prodrug or solvate thereof, that is effective in treating abnormal cell growth, and a pharmaceutically acceptable carrier.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs; and (4) any tumors that proliferate by virtue of farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The present invention relates to crystal forms of the following compound:

formula I

The present invention further relates to the two distinct crystal forms of the compound of formula I. The compound of formula I has been found to have two crystal forms, one form is an anhydrous, while the second is a sesquihydrate. The anhydrous crystal form of the compound of formula I is referred herein as crystal form A. The sesquihydrate crystal form of the compound of formula I is referred herein as crystal form B.

The invention further relates to a method for the preparation of the crystal forms of compound of formula I. Formula I is also identified herein as 6-[(4-chloro-phenyl)-hydroxy-(3-methyl-3H-imidazol-4-yl)-methyl]-4-(3-ethynyl-phenyl)-1-methyl-1H-quinolin-2-one, 2,3-dihydroxybutanedioate (1:1). The free base, 6-[(4-chloro-phenyl)-hydroxy-(3-methyl-3H-imidazol-4-yl)-methyl]-4-(3-ethynyl-phenyl)-1-methyl-1H-quinolin-2-one, has a chiral center at its 6-position and the enantiomers can rotate the plane of polarization in a clockwise (+) or counterclockwise (−) direction.

The compounds of the present invention are useful in the treatment of hyperproliferative diseases, such as cancers, in mammals, especially humans, and to pharmaceutical compositions containing such compounds.

The tartrate salt of the compound of formula I has unexpectedly found to have improved solubility in gastric fluids compared to other salts of the compound of formula I, i.e., HCl. Improved solubility in gastric fluids will make the tartrate salt of the compound of formula I more readily bioavailable when administered in tablet form.

The crystal forms of the compound of formula I have been characterized using powder X-ray diffractometry. The powder X-ray diffraction pattern for enantiomer pairs (+)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxybutanedioate and (−)-6-[(4-chloro-phenyl)-hydroxy-(3-methyl-3H-imidazol-4-yl)-methyl]4-(3-ethynyl-phenyl)-1-methyl-1H-quinolin-2-one, (+)-2,3-dihydroxybutanedioate or (+)-6-[(4-chloro-phenyl)-hydroxy-(3-methyl-3H-imidazol-4-yl)-methyl]-4-(3-ethynyl-phenyl)-1-methyl-1H-quinolin-2-one, (+)-2,3-dihydroxybutanedioate and (−)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxybutanedioate will be the same.

Figure 1:
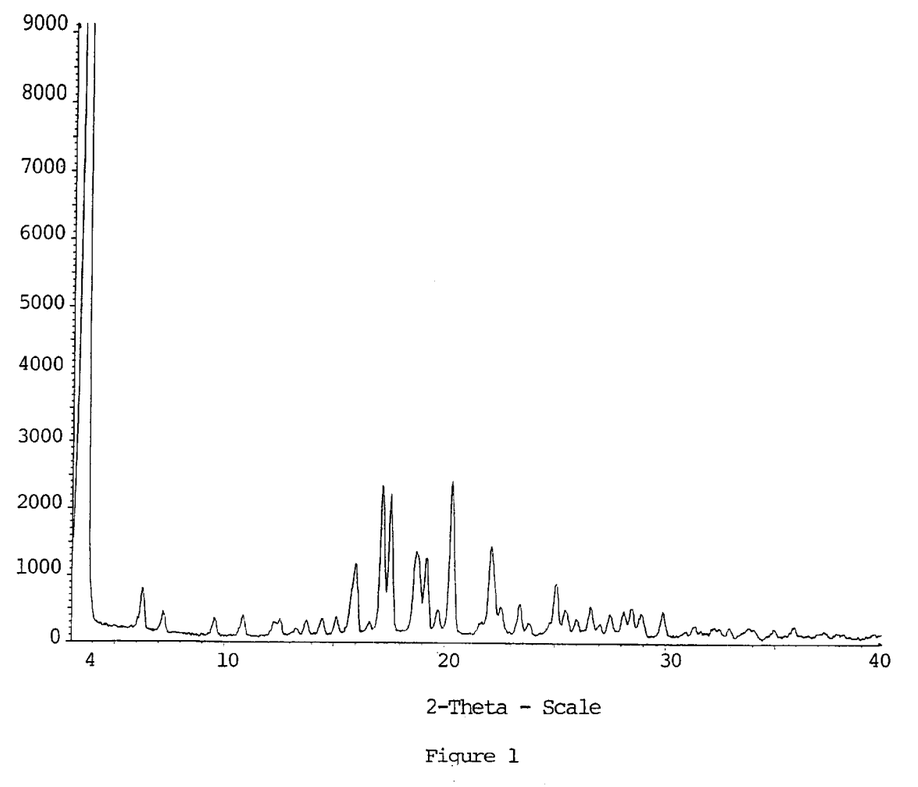
FIG. 1 shows a powder X-ray diffraction pattern for the anhydrous crystal form A of (+)-6-[(4-chloro-phenyl)-hydroxy-(3-methyl-3H-imidazol-4-yl)-methyl]-4-(3-ethynyl-phenyl)-1-methyl-1H-quinolin-2-one,(−)-2,3-dihydroxy butanedioate.
Figure 2:
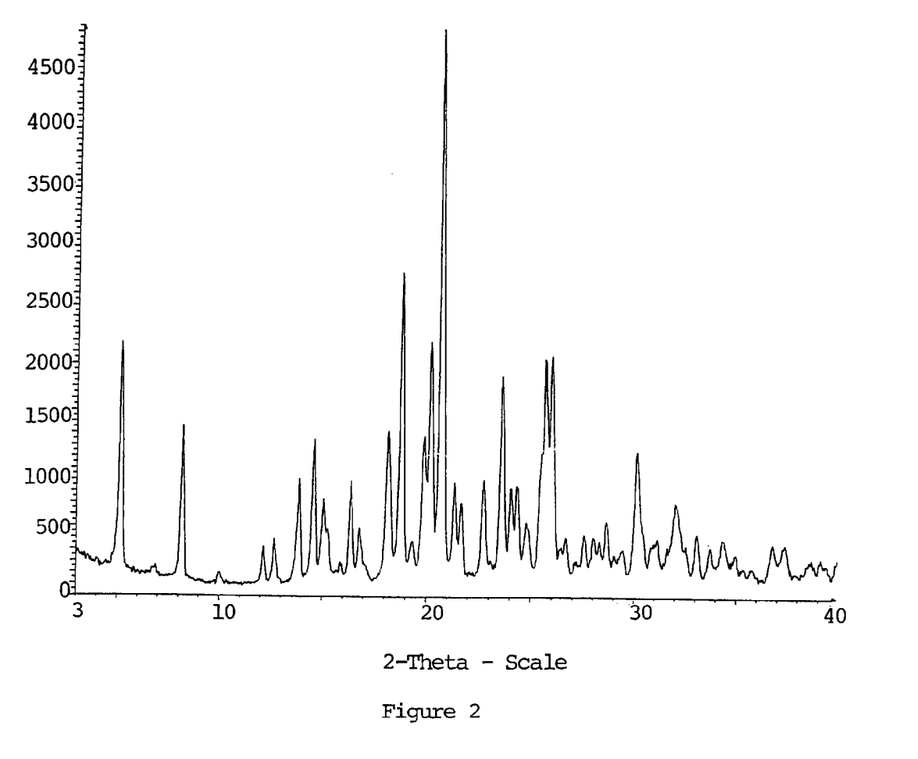
FIG. 2 shows a powder X-ray diffraction pattern for the hydrate crystal form B of (+)-6-[(4-chloro-phenyl)-hydroxy-(3-methyl-3H-imidazol-4-yl)-methyl]-4-(3-ethynyl-phenyl)-1-methyl-1H-quinolin-2-one,(−)-2,3-dihydroxy butanedioate.

Crystal form A of (±)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxybutanedioate provides a powder X-ray diffraction pattern substantially the same as shown in FIG. 1 Crystal form B of (+)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxybutanedioate provides a (powder X-ray diffraction pattern substantially the same as shown in FIG. 2. However, it is known that a powder X-ray diffraction pattern may be obtained with a measurement error depending on measurement conditions. In particular, it is generally known that intensities in a powder X-ray diffraction pattern may fluctuate depending on measurement conditions. Therefore, it should be understood that the crystal forms of the present invention are not limited to the crystals that provide a powder X-ray diffraction pattern completely identical to the powder X-ray diffraction patterns shown in FIGS. 1 and 2. Any crystal forms of formula I which provide a powder X-ray diffraction pattern substantially the same as the aforementioned powder X-ray diffraction patterns of FIGS. 1 and 2 fall within the scope of the present invention. Those skilled in the field of powder X-ray diffractometry can readily judge the substantial identity of powder X-ray diffraction patterns.

For example, the crystal form A of the present invention is characterized in that the crystal provides a high intensity diffraction peak at diffraction angle (2θ) of about 3.6 in a powder X-ray diffraction analysis. Generally, a measurement error of diffraction angle for a usual powder X-ray diffractometry is about 5% or less, and such degree of measurement error should be taken into account as to the aforementioned diffraction angles. Furthermore, it should be understood that relative intensities may fluctuate depending on experimental conditions as described above, and accordingly, the order of intensity should not be taken into account.

The compounds of formula I exhibit activity as Ras farnesylation inhibitors and are useful in the treatment of cancer and the inhibition of abnormal cell growth in mammals, including humans. The activity of the compounds of formula I as Ras farnesylation inhibitors may be determined by their ability, relative to a control, to inhibit Ras farnesyl transferase in vitro. This procedure is described below.

A crude preparation of human farnesyl transferase (FTase) comprising the cytosolic fraction of homogenized brain tissue is used for screening compounds in a 96-well assay format. The cytosolic fraction is prepared by homogenizing approx. 40 grams fresh tissue in 100 ml of sucrose/$MgCl_2$/EDTA buffer (using a Dounce homogenizer; 10–15 strokes), centrifuging the homogenates at 1000 grams for 10 minutes at 4G, re-centrifuging the supernatant at 17,000 grams for 15 minutes at 4G, and then collecting the resulting supernatant. This supernatant is diluted to contain a final concentration of 50 mM Tris HCl (pH 7.5), 5 mN DTT, 0.2 M KCl, 20 mM $ZnCl_2$, 1 mM PMSF and re-centrifuged at 178,000 grams for 90 minutes at 4G. The supernatant, termed "crude FTase" was assayed for protein concentration, aliquoted, and stored at −70° C.

The assay used to measure in vitro inhibition of human FTase is a modification of the method described by Amersham LifeScience for using their Farnesyl transferase (3H) Scintillation Proximity Assay (SPA) kit (TRKQ 7010). FTase enzyme activity is determined in a volume of 100 ml containing 50 mM N-(2-hydroxy ethyl) piperazine-N-(2-ethane sulfonic acid) (HEPES), pH 7.5, 30 mM $MgCl_2$, 20 uM KCl, 5 mM $Na_2HPO_4$, 5 mM dithiothreitol (DTT), 0.01% Triton X-100, 5% dimethyl sulfoxide (DMSO), 20 mg of crude FTase, 0.12 mM [3H]-farnesyl pyrophosphate ([3H]-FPP; 36000 dpm/pmole, Amersham LifeScience), and 0.2 mM of biotinylated Ras peptide KTKCVIS (Bt-KTKCVIS) that is N-terminally biotinylated at its alpha amino group and was synthesized and purified by HPLC in house. The reaction is initiated by addition of the enzyme and terminated by addition of EDTA (supplied as the STOP reagent in kit TRKQ 7010) following a 45 minute incubation at 37° C. Prenylated and unprenylated Bt-KTKCVIS is captured by adding 10 ml of steptavidin-coated SPA beads (TRKQ 7010) per well and incubating the reaction mixture for 30 minutes at room temperature. The amount of radioactivity bound to the SPA beads is determined using a MicroBeta 1450 plate counter. Under these assay conditions, the enzyme activity is linear with respect to the concentrations of the prenyl group acceptor, Bt-KTKCVIS, and crude FTase, but saturating with respect to the prenyl donor, FPP. The assay reaction time is also in the linear range.

The test compounds are routinely dissolved in 100% dimethyl sulfoxide (DMSO). Inhibition of farnesyl transferase activity is determined by calculating percent incorporation of tritiated-farnesyl in the presence of the test compound vs. its incorporation in control wells (absence of inhibitor). $IC_{50}$ values, that is, the concentration required to produce half maximal farnesylation of Bt-KTKCVIS, is determined from the dose-responses obtained.

Administration of the compounds of the present invention (also referred to herein as the "active compound(s)") can be effected by any method that enables delivery of the compounds to the site of action. These methods preferably include oral routes such as in the form of tablets or capsules, intraduodenal routes, parenteral injection (including intravenous, subcutaneous, intramuscular, intravascular or infusion), topical, and rectal administration. Oral administration is preferred for the crystal Form A. Particularly preferred routes of oral administration include tablets or capsules.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The following examples illustrate preparation of free base of formula I, 6-[(4-chloro-phenyl)- and the tartrate crystalline forms of the free base. The examples are not intended to limited the invention as defined hereinabove and as claimed below.

EXAMPLE 1

6-[(4-Chloro-phenyl)-hydroxy-(3-methyl-3H-imidazol-4-yl)-methyl]-4-(3-ethynyl-phenyl)-1-methyl-1H-quinolin-2-one 1A. 5-[2-(4-Chloro-phenyl)-[1,3]dioxolan-2-yl]-3-(3-iodo-phenyl)-benzo[c]isoxazole 2-(4-Chlorophenyl)-2-(4-nitrophenyl)-1,3-dioxolane (38.7 g, 127 mMol) was suspended in 190 mL of methanol (MeOH) under an atmosphere of dry $N_2$. To this solution was added (3-iodophenyl)acetonitrile (46.3 g, 190 mMol) and 25.4 g (625 mMol) of sodium hydroxide (NaOH). The solution was then heated to reflux and reacted at this temperature for 2 hours. The reaction mixture was cooled to ambient temperature and the MeOH was removed under vacuum. The resulting red oil was partitioned between dichloromethane (DCM) and 0.1 N aqueous NaOH. The DCM layer was washed successively with 0.1 N aqueous NaOH and then brine. The DCM layer was dried over $MgSO_4$, filtered and concentrated under vacuum to give a dark red oil. The oil was stirred in MeOH and the titled compound precipitated out as a yellow solid. The yellow solid was washed with MeOH and dried under vacuum to give 52.4 g of the titled compound which was used without further purification.

1B. [6-Amino-3-(4-chloro-benzoyl)-cyclohexa-2,4-dienyl]-(3-iodo-phenyl)-methanone 5-[2-(4-Chloro-phenyl)-[1,3]dioxolan-2-yl]-3-(3-iodo-phenyl)-benzo[c]isoxazole (65.4 g, 130 mMol) was dissolved in a solution of tetrahydrofuran (THF) (500 mL) and DCM (100 mL). To this solution, was added 500 mL of titanium(III) chloride (10 wt. % solution in 20–30 wt. % hydrochloric acid (HCl)) and the reaction mixture was stirred for 1 hour. An additional 100 mL of titanium(III) chloride (10 wt. % solution in 20–30 wt. % HCl) was added to the reaction mixture and the reaction mixture was stirred for 2.5 hours. The reaction mixture was then poured into ice water and the resulting heterogeneous solution was extracted with DCM. The DCM layer was successively washed with aqueous saturated $NaHCO_3$ and brine. The DCM layer was dried over $MgSO_4$, filtered and concentrated under vacuum to give titled compound as an orange oil (60 g). The oil was used without further purification.

1C. 6-(4-Chloro-benzoyl)-4-(3-iodo-phenyl)-1H-quinolin-2-one

[6-Amino-3-(4-chloro-benzoyl)-cyclohexa-2,4-dienyl]-(3-iodo-phenyl)-methan-one (60 g, 130 mMol) was dissolved in anhydrous toluene (450 mL) under an atmosphere of dry $N_2$. To this solution was added 180 mL of triethylamine ($NEt_3$), 50 mL of acetic anhydride ($Ac_2O$) and 1.60 g (13.0 mMol) of 4-dimethylaminopyridine (DMAP). The reaction mixture was then heated to reflux and stirred at this temperature for 20 hours. The reaction mixture was cooled to ambient temperature and the precipitate was collected via suction filtration. The solid was washed with ethyl ether ($Et_2O$) and dried under vacuum to give of the titled compound (63 g) which was used without further purification.

1D. 6-(4-Chloro-benzoyl)-4-(3-iodo-phenyl)-1-methyl-1H-quinolin-2-one 6-(4-Chloro-benzoyl)-4-(3-iodo-phenyl)-1H-quinolin-2-one (63 g, 130 mMol) was dissolved in THF (500 mL) under an atmosphere of dry $N_2$. To this solution, was added a 10 N aqueous NaOH (550 mL), benzyltriethylammonium chloride (13.8 g, 60.5 mMol) and methyl iodide (13.5 mL, 212.0 mMol). The reaction mixture was stirred at ambient temperature for 15 hours after which time it was partitioned between DCM and water. The DCM layer was successively washed with water (4 times) and then brine. The organic layer was dried over $MgSO_4$, filtered and concentrated under vacuum to give 51.2 g of a yellow solid as the titled compound which was used without further purification.

1E. 6-(4-Chloro-benzoyl)-1-methyl-4-(3-trimethylsilanylethynyl-phenyl)-1H-quinol in-2-one 6-(4-Chloro-benzoyl)-4-(3-iodo-phenyl)-1-methyl-1H-quinolin-2-one (9.98 g, 20.0 mMol) was suspended in diethylamine (300 mL). To this solution was added 50 mL of anhydrous N,N-dimethylformamide (DMF), (trimethylsilyl)acetylene (8.5 mL) and bis (triphenylphosphine)-palladium(II) chloride (1.40 g, 2.00 mMol). The flask was covered with aluminum foil and then copper(l) iodide (780 mg, 4.09 mMol) was added causing the reaction mixture to exotherm. After stirring overnight under an atmosphere of dry $N_2$ at ambient temperature, the reaction mixture was concentrated under vacuum and the residue was chromatographed on flash silica gel eluting with a gradient of DCM to MeOH/DCM (2:98) to give 8.55 g of the titled product as a solid.

1F. 6-[(4-Chloro-phenyl)-hydroxy-(2-mercapto-3-methyl-3H-imidazol-4-yl)-methyl]-1-methyl-4-(3-trimethylsilanylethynyl-phenyl)-1H-quinolin-2-one 2-Mercapto-1-methylimidazole (2.08 g, 18.2 mMol) was dissolved in anhydrous THF (200 mL) under an atmosphere of dry $N_2$. The solution was cooled to −78° C. and a solution of tert-butyl lithium (1.7 M in pentane, 22 mL, 37 mMol) was added. The solution was then warmed to 0° C. After a yellow precipitate formed, the solution was cooled to −78° C. and a solution of 6-(4-chloro-benzoyl)-1-methyl-4-(3-trimethylsilanyl ethynyl-phenyl)-1H-quinolin-2-one (8.55 g, 18.2 mmol) in anhydrous THF (25 mL) was added. After 30 minutes, the solution was warmed to 0° C. and stirred at this temperature for 1 hour. The reaction mixture was then warmed to ambient temperature and stirred overnight. The reaction was quenched with 20 mL of saturated aqueous ammonium chloride ($NH_4Cl$) and then partitioned between DCM and water. The DCM layer was dried over sodium sulfate ($Na_2SO_4$), filtered and concentrated under vacuum. The residue was chromatographed on flash silica gel eluting with a gradient from DCM to MeOH/DCM (3:97) to give 5.0 g of the titled compound as a solid.

1G. 6-[(4-Chloro-phenyl)-hydroxy-(3-methyl-3H-imidazol-4-yl)-methyl]-1-methyl-4-(3-trimethylsilanylethynyl-phenyl)-1H-quinolin-2-one 6-[(4-Chloro-phenyl)-hydroxy-(2-mercapto-3-methyl-3H-imidazol-4-yl)-methyl]-1-methyl-4-(3- trimethylsilanylethynyl-phenyl)-1H-quinolin-2-one (5.0 g, 8.6 mmol) was dissolved in ethanol (40 mL) to which was added Raney™ nickel (ca. 10 g) and the reaction was heated to reflux. More RANEY™ nickel was added every 20 minutes until mass spectral analysis of the reaction showed that the starting material had been consumed. The reaction mixture was cooled to ambient temperature and filtered through CELITE™ (diatomaceous earth). The CELITE™ was washed with copious amounts of ethanol. The filtrates were combined and concentrated under vacuum to give 3.88 g of the titled compound.

C.I. m/z 552 [M+1]; $^1$H NMR (CD$_3$OD) δ 7.64–7.75 (m, 3H), 7.17–7.48 (m, 9H), 6.59 (s, 1H), 6.17 (s, 1H), 3.79 (s, 3H), 3.42 (s, 3H), 0.23 (s, 9H).

1H. 6-[(4-Chloro-phenyl)-hydroxy-(3-methyl-3H-imidazol-4-yl)-methyl]-4-(3-ethynyl-phenyl)-1-methyl-1H-quinolin-2-one 6-[(4-Chloro-phenyl)-hydroxy-(3-methyl-3H-imidazol-4-yl)-methyl]-11-methyl-4-(3-trimethylsilanylethynyl-phenyl)-1H-quinolin-2-one (3.88 g, 7.03 mMol) was dissolved in THF (10 mL) under an atmosphere of dry N$_2$. To this solution was added a solution of 1.0 N tetrabutylammonium fluoride in THF (20 mL, 20 mMol). The reaction mixture was stirred overnight at ambient temperature and was then concentrated under vacuum. The residue was partitioned between 4-(dicyanomethylene)-2-methyl-6-(4-dimethylamino-styryl)-4H-pyran (DCM) and water. The DCM layer was saved and washed 3 more times with water and then with brine. The DCM layer was dried over Na$_2$SO$_4$, filtered and concentrated under vacuum. The residue was chromatographed on flash silica gel eluting with a gradient from DCM to MeOH/DCM (4:96) to give 3.01 g of the titled compound.

C.I. m/z 480 [M+1]; $^1$H NMR (CD$_3$OD) δ 7.75 (dd, J=2.1, 8.9 Hz, 1H), 7.69 (s, 1H), 7.66 (d, 8.5 Hz, 1H), 7.52 (d, J=7.9 Hz, 1H), 7.41 (t, J=7.7 Hz, 1H), 7.38 (s, 1H), 7.29 (m, 3H), 7.23 (d, J=1.7 Hz, 1H), 7.17 (d, J=8.5 Hz, 2H), 6.59 (s, 1H), 6.16 (s, 1H), 3.79 (s, 3H), 3.60 (s, 1H), 3.42 (s, 3H).

EXAMPLE 2

Separation of the Enantiomers of 6-[(4-Chloro-phenyl)-hydroxy-(3-methyl-3H-imidazol-4-yl)-methyl]-4-(3-ethynyl-phenyl)-1-methyl-1H-quinolin-2-one 6-[(4-Chloro-phenyl)-hydroxy-(3-methyl-3H-imidazol-4-yl)-methyl]-4-(3-ethynyl-phenyl)-1-methyl-1H-quinolin-2-one (4.96 g) was separated into its enantiomers and purified by high-performance liquid chromatography over CHIRAL-PAK™ AD (manufactured by Daicel Chemical Industries, LTD, Osaka, Japan) (20 μm; eluent: Hexane/isopropanol/diethylamine 85/15/0.1; 30° C.). Under these conditions, 1.73 g of the faster eluting enantiomer was obtained and 2.07 g of the slower moving enantiomer B. The slower moving enantiomer B has a specific rotation ($\{α\}_D^{20}$=+28.2 (c=10 mg/mL)) in ethanol. Both enantiomers were >97% optically pure.

EXAMPLE 3

(+)-6-[(4-chloro-phenyl)-hydroxy-(3-methyl-3H-imidazol-4-yl)-methyl]-4-(3-ethynyl-phenyl)-1-methyl-1H-quinolin-2-one,(−)-2,3-dihydroxy butanedioate (1:1), (Crystal Form B)

A 125 ml flask was charged with 3.8 gins (7.92 mmoles) of (+)-6-[(4-chloro-phenyl)-hydroxy-(3-methyl-3H-imidazol-4-yl)methyl-]4-(3-ethynyl-phenyl)-1-methyl-1H-quinolin-2-one and 57 ml of THF 95%/water 5% by weight. The mixture was stirred until a clear amber solution was obtained. The amber solution was then speck-free filtered into a speck-free 125 ml flask. Then 1.55 gins (10.3 mmoles) of D-(−)tartaric acid was added to the filtered solution while stirring. After stirring for 20 hours a thick slurry had formed. The solids were isolated by filtration and the filter cake washed with 16 mls of Ethyl acetate. The solids were dried by pulling vacuum on the filter, a small sample is vacuum dried at 40° C. for analysis resulting in crystal form B having the powder X-ray diffraction pattern shown in FIG. 2. Crystal form B was found to show plate/lath habit.

Using thermogravimetric analysis (TGA) form B lost approximately 5.5% weight at a temperature below 100° C., which is close to a seqsquihydrate (5.3%). Additionally, crystal form B was characterized as having a dehydration endotherm of between 80° C. and 100° C. using Differential Scanning Calorimetry (DSC).

EXAMPLE 4

(+)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxy butanedioate (1:1), (Crystal Form A)

The filter cake (Form B) from Example 3 was placed in a 500 ml flask and 160 mls of dry ethyl acetate was added and the stirred suspension was atmospherically distilled. As solvent distilled off fresh ethyl acetate was added until a total of 320 mls of dry ethyl acetate had been added, the final volume of the reaction was 80 mls. The reaction mixture was granulated for 20 hrs at ambient temperature.

The solids were isolated by filtration and the filter cake washed with 30 mls of ethyl acetate followed by vacuum drying at 40° C., resulting in the recovery of crystal form A having the powder X-ray diffraction pattern shown in FIG. 1.

Crystal form A was found to melt with a small endotherm followed by decomposition with an exotherm peak temperature of 189° C. by DSC.

What is claimed is:

1. A crystal form of 6-[(4-chloro-phenyl)-hydroxy(3-methyl-3H-imidazol-4-yl)-methyl]-4-(3-ethynyl-phenyl)-1-methyl-1H-quinolin-2-one, 2,3-dihydroxy butanedioate anhydrous salt.

2. The crystal form according to claim 1, comprising high-intensity diffraction peaks at diffraction angles (2θ) of about 3.6, 17.2, 17.6, 18.8, 19.2, 20.4 and 22.1 in the powder X-ray diffraction analysis.

3. The crystal form according to claim 2, comprising a powder X-ray diffraction pattern having characteristic peaks expressed in degrees (2θ) at approximately:

| Angle 2 theta | Angle 2 theta | Angle 2 theta |
|---|---|---|
| 3.6 | 16.9 | 23.4 |
| 6.2 | 17.2 | 25.1 |
| 7.2 | 17.6 | 25.5 |
| 9.5 | 18.8 | 26.0 |
| 10.8 | 19.2 | 26.7 |
| 12.3 | 19.7 | 27.6 |
| 12.5 | 20.4 | 28.2 |
| 13.8 | 21.7 | 28.5 |

-continued

| Angle 2 theta | Angle 2 theta | Angle 2 theta |
|---|---|---|
| 14.5 | 22.1 | 29.0 |
| 16.0 | 22.6 | 29.9. |

4. The crystal form according to claim 3, wherein said salt has a powder X-ray diffraction pattern substantially the same as the powder X-ray diffraction pattern shown in FIG. 1.

5. The crystal form according to claim 1, wherein said anhydrous salt is (+)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxy butanedioate.

6. The crystal form according to claim 1, wherein said anhydrous salt is 6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxy butanedioate.

7. The crystal form according to claim 5, wherein said anhydrous salt is (+)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxy butanedioate.

8. The crystal form according to claim 1, wherein said anhydrous salt is (−)-6-[(4-chloro-phenyl)-hydroxy-(3-methyl-3H-imidazol-4-yl)-methyl]-4-(3-ethynyl-phenyl)-1-methyl-1H-quinolin-2-one, 2,3-dihydroxy butanedioate.

9. The crystal form according to claim 1, wherein said anhydrous salt is 6-[(4-chloro-phenyl)-hydroxy-(3-methyl-3H-imidazol-4-yl)-methyl]-4-(3-ethynyl-phenyl)-1-methyl-1H-quinolin-2-one, (±)-2,3-dihydroxy butanedioate.

10. The crystal form according to claim 9, wherein said anhydrous salt is (−)-6-[(4-chloro-phenyl)-hydroxy-(3-methyl-3H-imidazol-4-yl)-methyl]-4-(3-ethynyl-phenyl)-1-methyl-1H-quinolin-2-one, (±)-2,3-dihydroxy butanedioate.

11. The crystal form according to claim 1, wherein said anhydrous salt has a melting point of 189° C.

12. A crystal form of 6-[(4-chloro-phenyl)-hydroxy-(3-methyl-3H-imidazol-4-yl)-methyl]-4-(3-ethynyl-phenyl)-1-methyl-1H-quinolin-2-one, 2,3-dihydroxy butanedioate hydrate salt.

13. The crystal form according to claim 12, comprising high-intensity diffraction peaks at diffraction angles (2θ) of about 5.1, 8.1, 18.2, 18.8, 20.2, 20.8, 23.6, 25.8 and 26.0 in the powder X-ray diffraction analysis.

14. The crystal form according to claim 13, comprising a powder X-ray diffraction pattern having characteristic peaks expressed in degrees (2θ) at approximately:

| Angle 2-theta | Angle 2-theta | Angle 2-theta |
|---|---|---|
| 5.1 | 19.9 | 26.0 |
| 8.1 | 20.2 | 26.7 |
| 12.7 | 20.8 | 27.6 |
| 13.9 | 21.4 | 28.1 |
| 14.6 | 21.7 | 28.7 |
| 15.2 | 22.8 | 30.2 |
| 15.3 | 23.6 | 31.2 |
| 16.4 | 24.1 | 32.1 |
| 16.8 | 24.4 | 33.1 |
| 18.2 | 24.8 | 34.4 |
| 18.8 | 25.5 | 36.8 |
| 19.3 | 25.8 | 37.4. |

15. The crystal form according to claim 14, wherein said crystal form has a powder X-ray diffraction pattern substantially the same as the powder X-ray diffraction pattern shown in FIG. 2.

16. The crystal form according to claim 12, wherein said hydrate is (+)-6[(4-chloro-phenyl)-hydroxy-(3-methyl-3H-imidazol-4-yl)-methyl]-4-(3-ethynyl-phenyl)-1-methyl-1H-quinolin-2-one, 2,3-dihydroxy butanedioate.

17. The crystal form according to claim 12, wherein said hydrate is 6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxy butanedioate.

18. The crystal form according to claim 17, wherein said hydrate is (+)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxy butanedioate.

19. The crystal form according to claim 12, wherein said hydrate is (−)-6-[(4-chloro-phenyl)-hydroxy-(3-methyl-3H-imidazol-4-yl)-methyl]-4-(3-ethynyl-phenyl)-1-methyl-1H-quinolin-2-one, 2,3-dihydroxy butanedioate.

20. The crystal form according to claim 12, wherein said hydrate is 6-[(4-chloro-phenyl)-hydroxy-(3-methyl-3H-imidazol-4-yl)-methyl]-4-(3-ethynyl-phenyl)-1-methyl-1H-quinolin-2-one, (+)-2,3-dihydroxy butanedioate.

21. The crystal form according to claim 20, wherein said hydrate is (−)-6-[(4-chloro-phenyl)-hydroxy-(3-methyl-3H-imidazol-4-yl)-methyl]-4-(3-ethynyl-phenyl)-1-methyl-1H-quinolin-2-one, (+)-2,3-dihydroxy butanedioate.

22. A process for preparing a salt having the formula comprising treating 6-[(4-chloro-phenyl)-hydroxy-(3-methyl-3H-imidazol-4-yl)-methyl]-4-(3-ethynyl-phenyl)-1-methyl-1H-quinolin-2-one with tartaric acid which provides high-intensity diffraction peaks at diffraction angles (2θ) of 5.1, 8.1, 18.2, 18.8, 20.2, 20.8, 23.6, 25.8 and 26.0 in the powder X-ray diffraction pattern.

23. The process of claim 22, wherein said process is carried out in a mixture of THF and water.

24. The process of claim 22, wherein said salt is (+)-6-[(4-chloro-phenyl)-hydroxy-(3-methyl-3H-imidazol-4-yl)-methyl]-4-(3-ethynyl-phenyl)-1-methyl-1H-quinolin-2-one, (−)-2,3-dihydroxy butanedioate hydrate salt.

25. The process of claim 22, wherein said salt is (−)-6-[(4-chloro-phenyl)-hydroxy-(3-methyl-3H-imidazol-4-yl)-methyl]-4-(3-ethynyl-phenyl)-1-methyl-1H-quinolin-2-one, (+)-2,3-dihydroxy butanedioate hydrate salt.

26. A pharmaceutical composition comprising a therapeutically effective amount of a compound of claim 1 and a pharmaceutically acceptable carrier.

* * * * *